(12) United States Patent
Marcotulli et al.

(10) Patent No.: US 11,260,069 B2
(45) Date of Patent: Mar. 1, 2022

(54) NICOTINAMIDE RIBOSIDE AND PTEROSTILBENE COMPOSITIONS AND METHODS FOR TREATMENT OF NEURODEGENERATIVE DISORDERS

(71) Applicant: Elysium Health, Inc., New York, NY (US)

(72) Inventors: Eric Alexander Marcotulli, New York, NY (US); Daniel Antonio Alminana, New York, NY (US)

(73) Assignee: Elysium Health, Inc., New York, NY (US)

( * ) Notice: Subject to any disclaimer, the term of this patent is extended or adjusted under 35 U.S.C. 154(b) by 0 days.

(21) Appl. No.: 16/327,651

(22) PCT Filed: Aug. 22, 2017

(86) PCT No.: PCT/US2017/047979
§ 371 (c)(1),
(2) Date: Feb. 22, 2019

(87) PCT Pub. No.: WO2018/039207
PCT Pub. Date: Mar. 1, 2018

(65) Prior Publication Data
US 2019/0201426 A1 Jul. 4, 2019

Related U.S. Application Data

(60) Provisional application No. 62/378,053, filed on Aug. 22, 2016.

(51) Int. Cl.
| | | |
|---|---|---|
| *A61K 31/706* | (2006.01) | |
| *A61K 31/09* | (2006.01) | |
| *A61P 25/16* | (2006.01) | |
| *A61P 25/20* | (2006.01) | |
| *A61P 25/28* | (2006.01) | |

(52) U.S. Cl.
CPC ............ *A61K 31/706* (2013.01); *A61K 31/09* (2013.01); *A61P 25/16* (2018.01); *A61P 25/28* (2018.01)

(58) Field of Classification Search
CPC ....... A61K 31/706; A61K 31/09; A61P 25/28; A61P 25/16
USPC ......................................................... 514/43
See application file for complete search history.

(56) References Cited

U.S. PATENT DOCUMENTS

2012/0165412 A1 6/2012 van der Beek et al.
2013/0296440 A1 11/2013 Bartos

FOREIGN PATENT DOCUMENTS

| CN | 1964627 A | | 5/2007 |
|---|---|---|---|
| CN | 102958516 A | | 3/2013 |
| EP | 2574339 A1 | | 4/2013 |
| EP | 2805719 A1 | | 11/2014 |
| JP | 2008/501343 A | | 1/2008 |
| JP | 2014/514361 A | | 6/2014 |
| RU | 2576032 C2 | | 2/2016 |
| WO | WO-2009/032870 A2 | | 3/2009 |
| WO | WO-2013090557 A2 | | 6/2013 |
| WO | WO 2015/066382 | * | 5/2015 |
| WO | WO-2015/186068 A1 | | 12/2015 |
| WO | WO-2016122832 A1 | | 8/2016 |
| WO | WO 2016/149277 | * | 9/2016 |

OTHER PUBLICATIONS

Glossary of medical education terms, Institute of International Medical Education. http://www.iime.org/glossary.htm Accessed in Mar. 2013. (Year: 2013).*
Bedlack et al. ALSUntangled 42: Elysium health's "basis". Amyotrophic Lateral Sclerosis and Frontotemporal Degeneration, 2018; 19: 317-319. (Year: 2018).*
Bieganowski et al., "Discoveries of nicotinamide riboside as a nutrient and conserved NRK genes establish a preiss-handler independent route to NAD+ in fungi and humans," Cell 117:495-502 (2004).
International Search Report and Written Opinion in International Application No. PCT/US2017/047979 dated Oct. 25, 2017.
Extended European Search Report for EP Application No. EP 17844270 dated Feb. 13, 2020.
Chang et al., "Low-dose pterostilbene, but not resveratrol, is a potent neuromodulator in aging and Alzheimer's disease," Neurobiology of Aging, 33: 2062-2071 (2012).

* cited by examiner

*Primary Examiner* — Yih-Horng Shiao
(74) *Attorney, Agent, or Firm* — Foley Hoag LLP; Brendan T. Jones; Allison Gilder

(57) ABSTRACT

Compositions containing a combination of nicotinamide riboside and pterostilbene for treating neurodegenerative disorders, and methods of treating neurodegenerative disorders using these compositions and their equivalents are described. The neurodegenerative disorders that can be treated using these compositions or methods can include parkinson's disease, huntington's disease, alzheimer's disease, and the like. In an embodiment, the compositions containing a combination of nicotinamide riboside and pterostilbene can be prepared as oral formulations. In some embodiments, a dietary supplement comprises nicotinamide riboside and/or pterostilbene or equivalents.

10 Claims, No Drawings

NICOTINAMIDE RIBOSIDE AND PTEROSTILBENE COMPOSITIONS AND METHODS FOR TREATMENT OF NEURODEGENERATIVE DISORDERS

RELATED APPLICATIONS

This application is a § 371 national-stage application based on PCT/US17/47979, filed Aug. 22, 2017, which claims the benefit of priority to U.S. Provisional Patent Application Ser. No. 62/378,053, filed Aug. 22, 2016, each of which is incorporated by reference in its entirety.

FIELD OF THE INVENTION

The field of the invention generally relates to compositions and methods for the treatment of neurodegenerative disorders. Embodiments of the invention relate to nicotinamide riboside and pterostilbene compositions and methods for treatment of neurodegenerative disorders.

BACKGROUND OF THE INVENTION

Neurodegenerative disorders are prevalent and can often produce symptoms that greatly inhibit those with the disorder. Neurodegenerative disorders manifest themselves in many ways but often produce symptoms such as tremors, altered posture, dementia, memory loss, and speech problems. Often, neurodegenerative disorders produce impaired motor capabilities. Certain disorders can be hereditary or caused by environmental factors. Certain disorders such as Parkinson's disease may be caused by prions.

Prior art treatments of these neurodegenerative disorders have failed to treat the disorder or adequately alleviate the symptoms. For example, reducing the death of dopaminergic neurons can maintain the body's natural production of dopamine, which plays an important role in motor functions along with feelings of gratification. Certain disorders such as Parkinson's disease have relied on treatments of administration of Levodopa (L-DOPA), which is a precursor to dopamine and increases the dopamine concentration in the human brain.

Seven mammalian sirtuin enzymes, SIRT1-7, play an important role in maintaining metabolic homeostasis in multiple tissues. SIRT1-7 exhibit distinctive enzymatic activities, tissue and subcellular localization, and have been characterized as antiaging proteins. The sirtuins function by translating changes in nutritional state to metabolic adaptations.

Sirtuin 1, (SIRT1), is a nicotinamide adenine dinucleotide (NAD+) dependent deacetylase. SIRT1 mediates p53 dependent processes, transcription regulation, muscle differentiation, adipogenesis, and protection of neurons and their axons from degeneration. SIRT1 also participates in early embryogenesis, neurogenesis, and cardiogenesis.

Sirtuin 2 (SIRT2) is an evolutionarily conserved NAD+ dependent hi stone/protein deacetylase that tightly couples the cleavage of NAD+ and the deacetylation of protein substrates.

Without being hound by theory, sirtuin enzymes are believed to act by transferring an acetyl group from their substrate protein to the ADP-ribose moiety of NAD+. It is believed this cleaves the coenzyme and releases nicotinamide and O-acetyl-ADP-ribose. The mechanism of action of sirtuins appears to involve regulating transcription through deacetylating histones and altering nucleosome structure. It is also believed that non-histone proteins can be deacetylated by sirtuins. NAD+ is an important cofactor regulating metabolic homeostasis and believed to be a rate-limiting substrate for sirtuin deacetylases. Prior art treatments for certain neurodegenerative disorders includes administering medications and surgery, but these have only reduced some symptoms. Prior art treatments have failed to produce adequate beneficial results for neurodegenerative disorders, and needs exist for improved treatments for neurodegenerative disorders and/or symptoms of neurodegenerative disorders. While the body's homeostatic levels of NAD+ are generally stable, we have found that levels can be increased by providing supplementation of NAD+ via NAD+ precursors over what would be expected in the diet. Accordingly, embodiments of the invention and claims are intended to provide NAD+ precursors and/or sirtuin activators as a supplement or an active pharmaceutical ingredient and not as a normal food. The addition of NAD+ precursors to amounts that can increase the level of NAD+ in the body, certain tissues, or cellular compartmentalization can lead to beneficial effects over the amount normally consumed or located in these structures.

DETAILED DESCRIPTION OF THE INVENTION

Provided herein are methods and compositions related to treating and/or preventing a neurodegenerative disease or disorder and/or slowing the progression of a neurodegenerative disease or disorder in a subject by administering to the subject (e.g., orally administering to the subject) a composition comprising a compound of Formula I or Formula II (e.g., nicotinamide riboside), and/or a compound of Formula III (e.g., pterostilbene). The neurodegenerative disease or disorder may be Alzheimer's disease, Huntington's disease, Parkinson's disease, dementia, diabetes, or a disease or disorder associated with aging.

In certain aspects, the methods and compositions provided herein relate to treating and/or preventing Alzheimer's disease in a subject by administering to the subject (e.g., orally administering to the subject) a composition comprising a compound of Formula I or Formula II (e.g., nicotinamide riboside) and/or a compound of Formula III (e.g., pterostilbene).

In certain aspects, the methods and compositions provided herein relate to treating and/or preventing Huntington's disease in a subject by administering to the subject (e.g., orally administering to the subject) a composition comprising a compound of Formula I or Formula II (e.g., nicotinamide riboside) and/or a compound of Formula III (e.g., pterostilbene).

In certain aspects, the methods and compositions provided herein relate to treating and/or preventing Parkinson's disease in a subject by administering to the subject (e.g., orally administering to the subject) a composition comprising a compound of Formula I or Formula II (e.g., nicotinamide riboside) and/or a compound of Formula III (e.g., pterostilbene). Also provided herein are methods of treating, reducing the risk of, and/or reducing the prevalence of indicia (e.g., indicia disclosed herein) of a neurodegenerative disease in a subject by administering to the subject (e.g., orally administering to the subject) a composition comprising a compound of Formula I or Formula II (e.g., nicotinamide riboside) and/or a compound of Formula III (e.g., pterostilbene). Indicia of neurodegenerative disease may be tremors, resting tremors, bradykinesia, NAD+ content, sirtuin activity, limb rigidity, Lewy bodies, postural instability, freezing of gait, micrographia, reduced facial expression, uncontrolled movements, movement that is abnormally fast or slow, stooped posture, dystonia, impaired fine motor dexterity, impaired motor coordination, impaired gross motor coordination, decreased arm swing, akathisia, speech problems, softness of voice or slurred speech, difficulty swallowing, sexual dysfunction, cramping, drooling, excess saliva, loss of sense of smell, constipation, REM behavior disorder, mood disorder, orthostatic hypotension, sleep disturbances, vision problems, fatigue, loss of energy, depression, cognitive issues such as memory issues, slowed thinking, confusion, death of dopaminergic neurons, reduced dopamine concentration, prion occurrence, or dementia.

In certain embodiments of the compositions and methods provided herein, the composition comprises a compound of Formula I or Formula II (e.g., nicotinamide riboside) (e.g., at least 50 mg, at least 75 mg, at least 100 mg, at least 125 mg, at least 150 mg, at least 175 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 525 mg, at least 550 mg, at least 575 mg, at least 600 mg, at least 625 mg, at least 650 mg, at least 675 mg, at least 700 mg, at least 725 mg, at least 750 mg, at least 775 mg, at least 800 mg, at least 825 mg, at least 850 mg, at least 875 mg, at least 900 mg, at least 925 mg, at least 950 mg, at least 975 mg, at least 1000 mg, at least 1050 mg, at least 1100 mg, at least 1150 mg, at least 1200 mg, at least 1250 mg, at least 1300 mg, at least 1350 mg, at least 1400 mg, at least 1450 mg, or at least 1500 mg, of a compound of Formula I or Formula II (e.g., nicotinamide riboside)). In some embodiments, the composition comprises a compound of Formula III (e.g., pterostilbene) (e.g., at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 125 mg, at least 150 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 525 mg, at least 550 mg, at least 575 mg, at least 600 mg, at least 650 mg, at least 675 mg, at least 700 mg, at least 725 mg, at least 750 mg, at least 775 mg, at least 800 mg, at least 825 mg, at least 850 mg, at least 875 mg, at least 900 mg, at least 925 mg, at least 950 mg, at least 975 mg, at least 975 mg, or at least 1000 mg of a compound of Formula III (e.g., pterostilbene)). In certain embodiments, the composition comprises both a compound of Formula I or Formula II (e.g., nicotinamide riboside) (e.g., at least 50 mg, at least 75 mg, at least 100 mg, at least 125 mg, at least 150 mg, at least 175 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 525 mg, at least 550 mg, at least 575 mg, at least 600 mg, at least 650 mg, at least 675 mg, at least 700 mg, at least 725 mg, at least 750 mg, at least 775 mg, at least 800 mg, at least 825 mg, at least 850 mg, at least 875 mg, at least 900 mg, at least 925 mg, at least 950 mg, at least 975 mg, at least 1000 mg, at least 1050 mg, at least 1100 mg, at least 1150 mg, at least 1200 mg, at least 1250 mg, at least 1300 mg, at least 1350 mg, at least 1400 mg, at least 1450 mg, or at least 1500 mg of a compound of Formula I or Formula II (e.g., nicotinamide riboside)) and a compound of Formula III (e.g., pterostilbene) (e.g., at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 125 mg, at least 150 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 525 mg, at least 550 mg, at least 575 mg, at least 600 mg, at least 650 mg, at least 675 mg, at least 700 mg, at least 725 mg, at least 750 mg, at least 775 mg, at least 800 mg, at least 825 mg, at least 850 mg, at least 875 mg, at least 900 mg, at least 925 mg, at least 950 mg, at least 975 mg, or at least 1000 mg of a compound of Formula III (e.g., pterostilbene)).

In certain embodiments, the method comprises administering a plurality of doses of the composition. In some embodiments, at least 7 doses of the composition are administered. In some embodiments, at least 30 doses of the composition are administered. In some embodiments, at least 60 or more doses of the composition are administered. In some embodiments, each dose comprises at least 50 mg, at least 75 mg, at least 100 mg, at least 125 mg, at least 150 mg, at least 175 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 525 mg, at least 550 mg, at least 575 mg, at least 600 mg, at least 650 mg, at least 675 mg, at least 700 mg, at least 725 mg, at least 750 mg, at least 775 mg, at least 800 mg, at least 825 mg, at least 850 mg, at least 875 mg, at least 900 mg, at least 925 mg, at least 950 mg, at least 975 mg, at least 1000 mg, at least 1050 mg, at least 1100 mg, at least 1150 mg, at least 1200 mg, at least 1250 mg, at least 1300 mg, at least 1350 mg, at least 1400 mg, at least 1450 mg, or at least 1500 mg of a compound of Formula I or Formula II (e.g., nicotinamide riboside). In some embodiments, each dose comprises at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 125 mg, at least 150 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 525 mg, at least 550 mg, at least 575 mg, at least 600 mg, at least 650 mg, at least 675 mg, at least 700 mg, at least 725 mg, at least 750 mg, at least 775 mg, at least 800 mg, at least 825 mg, at least 850 mg, at least 875 mg, at least 900 mg, at least 925 mg, at least 950 mg, at least 975 mg, or at least 1000 mg of a compound of Formula III (e.g., pterostilbene).

In certain embodiments, each dose comprises at least 50 mg, at least 75 mg, at least 100 mg, at least 125 mg, at least 150 mg, at least 175 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 525 mg, at least 550 mg, at least 575 mg, at least 600 mg, at least 650 mg, at least 675 mg, at least 700 mg, at least 725 mg, at least 750 mg, at least 775 mg, at least 800 mg, at least 825 mg, at least 850 mg, at least 875 mg, at least 900 mg, at least 925 mg, at least 950 mg, at least 975 mg, at least 1000 mg, at least 1050 mg, at least 1100 mg, at least 1150 mg, at least 1200 mg, at least 1250 mg, at least 1300 mg, at least 1350 mg, at least 1400 mg, at least 1450 mg, or at least 1500 mg of a compound of Formula I or Formula II (e.g., nicotinamide riboside) and at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 125 mg, at least 150 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 525 mg, at least 550 mg, at least 575 mg, at least 600 mg, at least 650 mg, at least 675 mg, at least 700 mg, at least 725 mg, at least 750 mg, at least 775 mg, at least 800 mg, at least 825 mg, at least 850 mg, at least 875 mg, at least 900 mg, at least 925 mg, at least 950 mg, at least 975 mg, or at least 1000 mg of a compound of Formula III (e.g., pterostilbene).

In certain embodiments, a dose of the composition is administered at regular intervals over a period of time. In some embodiments, a dose of the composition is administered at least once a week. In some embodiments, a dose of the composition is administered at least twice a week. In certain embodiments, a dose of the composition is administered at least three times a week. In some embodiments, a dose of the composition is administered at least once a day. In some embodiments, a dose of the composition is administered at least twice a day. In some embodiments, doses of the composition are administered for at least 1 week, for at least 2 weeks, for at least 3 weeks, for at least 4 weeks, for at least 1 month, for at least 2 months, for at least 3 months, for at least 4 months, for at least 5 months, for at least 6 months, or for at least 1 year. In some embodiments, administration of the composition comprises administration of the composition in one or more dose(s). In some embodiments, administration of the composition comprises administration of the composition in one or more, five or more, ten or more, twenty or more, thirty or more, forty or more, fifty or more, one hundred or more, or one thousand or more dose(s). The compositions disclosed herein may be administered over any period of time effective to achieve the desired therapeutic response for a particular patient, composition, and mode of administration, without being toxic to the patient. The period of time may be at least 1 day, at least 10 days, at least 20 days, at least 30, days, at least 60 days, at least three months, at least six months, at least a year, at least three years, at least five years, or at least ten years. The dose may be administered when needed, sporadically, or at regular intervals. For example, the dose may be administered monthly, weekly, biweekly, triweekly, once a day, or twice a day.

In certain embodiments, the composition is formulated for oral delivery. In some embodiments, the composition is formulated as a pill, a tablet, or a capsule. In some embodiments, the composition is administered orally. In certain embodiments, the composition is self-administered.

Some embodiments may include a composition comprising a combination of a therapeutically effective amount of nicotinamide riboside and a therapeutically effective amount of pterostilbene; and a pharmaceutically acceptable excipient, wherein the combination is in a therapeutically effective amount for treatment of a neurodegenerative disorder.

Certain embodiments may include a method comprising administering a combination of a therapeutically effective amount of nicotinamide riboside and a therapeutically effective amount of pterostilbene for treatment of a neurodegenerative disorder in a patient in need of treatment thereof. In many cases, a precursor of nicotinamide riboside can be used to create a therapeutically effective amount of nicotinamide riboside. In some embodiments, a precursor of nicotinamide riboside can be used to create an effective amount of nicotinamide riboside.

Some embodiments may include oral formulations and methods of treating neurodegenerative disorders. In certain embodiments, a composition may contain a therapeutically effective amount of nicotinamide riboside, a therapeutically effective amount of pterostilbene, or both. In certain embodiments, a composition may comprise nicotinamide riboside and pterostilbene. In certain embodiments, a method may include administering a therapeutically effective amount of nicotinamide riboside and/or pterostilbene. In certain embodiments, a method may include orally administering a therapeutically effective amount of a combination of nicotinamide riboside and pterostilbene. In certain embodiments, a method may include orally administering a therapeutically effective amount of a combination of nicotinamide riboside and pterostilbene to treat a neurodegenerative disorder.

In certain embodiments, a composition may contain a therapeutically effective amount of nicotinamide riboside, a therapeutically effective amount of pterostilbene, or both. In certain embodiments, a method may include administering an effective amount of nicotinamide riboside and/or pterostilbene.

In certain embodiments, nicotinamide riboside may be administered in an amount of between about 100 mg and about 1000 mg per day. Nicotinamide riboside may be administered in combination with pterostilbene and said pterostilbene may be administered in an amount of between about 25 mg and about 500 mg per day.

In certain embodiments, nicotinamide riboside may be administered in an amount of between about 200 mg and about 700 mg per day. Nicotinamide riboside may be administered in combination with pterostilbene and said pterostilbene may be administered in an amount of between about 25 mg and about 250 mg per day.

In certain embodiments, nicotinamide riboside may be administered in an amount of about 250 mg per day. Nicotinamide riboside may be administered in combination with pterostilbene and said pterostilbene may be administered in an amount of between about 25 mg and about 250 mg per day. In certain embodiments, nicotinamide riboside may be administered in an amount of about 250 mg per day. Nicotinamide riboside may be administered in combination with pterostilbene and said pterostilbene may be administered in an amount of about 50 mg per day.

Certain embodiments may include administering a therapeutically effective amount of nicotinamide riboside and/or pterostilbene to increase a human's sirtuin activity. Certain embodiments may include administering a therapeutically effective amount of nicotinamide riboside and/or pterostilbene to increase a human's brain sirtuin activity.

Certain embodiments may include administering a therapeutically effective amount of nicotinamide riboside and/or pterostilbene to increase cellular NAD+ concentration. Certain embodiments may include administering a therapeutically effective amount of nicotinamide riboside and/or pterostilbene to increase muscle NAD+ concentration. Certain embodiments may include administering a therapeutically effective amount of nicotinamide riboside and/or pterostilbene to increase brain NAD+ concentration. Certain embodiments may include administering a therapeutically effective amount of nicotinamide riboside and/or pterostilbene to increase mitochondrial NAD+ concentration. Certain embodiments may include increasing NAD+ concentration in a human.

Certain embodiments comprise a sirtuin activating composition wherein said composition may comprise a therapeutically effective amount of nicotinamide riboside and/or pterostilbene.

Certain embodiments may include administering a therapeutically effective amount of nicotinamide riboside and/or pterostilbene to increase the uptake of certain neurotransmitters such as, but not limited to, dopamine.

Certain embodiments may include administering an effective amount of nicotinamide riboside and/or pterostilbene to maintain normal or healthy cellular NAD+ concentration. Certain embodiments may include administering an effective amount of nicotinamide riboside and/or pterostilbene to maintain normal or healthy NAD+ concentration. Certain embodiments may include administering an effective amount of nicotinamide riboside and/or pterostilbene to maintain normal or healthy brain NAD+ concentration. Certain embodiments may include administering an effective amount of nicotinamide riboside and/or pterostilbene to maintain normal or healthy mitochondrial NAD+ concentration. Certain embodiments may include increasing NAD+ concentration in a human. Certain embodiments may include maintaining a normal or healthy NAD+ concentration in a human.

Certain embodiments comprise a sirtuin activating composition wherein said composition may comprise an effective amount of nicotinamide riboside and/or pterostilbene and said composition maintains a normal or healthy level of sirtuin activity. Certain embodiments may include increasing sirtuin activity in a human. Certain embodiments may include maintaining a normal or healthy sirtuin activity in a human.

Certain embodiments may include administering an effective amount of nicotinamide riboside and/or pterostilbene to maintain a normal or healthy uptake of certain neurotransmitters such as, but not limited to, dopamine. Certain embodiments may include increasing neurotransmitter uptake in a human. Certain embodiments may include maintaining a normal or healthy uptake of neurotransmitters in a human.

Certain embodiments comprise an effective amount of nicotinamide riboside and/or pterostilbene and said composition maintains a normal or healthy level of cellular detoxification. Certain embodiments may include increasing cellular detoxification in a human. Certain embodiments may include maintaining a normal or healthy cellular detoxification in a human.

Some embodiments may include a composition comprising a therapeutically effective amount of nicotinamide mononucleotide and a therapeutically effective amount of epsilon-viniferin; and a pharmaceutically acceptable excipient, wherein the composition is in a therapeutically effective amount for treatment of a neurodegenerative disorder.

Certain embodiments may include a method comprising administering a therapeutically effective amount of nicotinamide mononucleotide and a therapeutically effective amount of epsilon-viniferin for treatment of a neurodegenerative disorder in a patient in need of treatment thereof.

Certain embodiments may include a composition comprising a therapeutically effective amount of nicotinamide mononucleotide and a therapeutically effective amount of niacin; and a pharmaceutically acceptable excipient, wherein the composition is in a therapeutically effective amount for treatment of a neurodegenerative disorder.

Some embodiments may include a method comprising administering a therapeutically effective amount of nicotinamide mononucleotide and a therapeutically effective amount of niacin for treatment of a neurodegenerative disorder in a patient in need of treatment thereof.

Some embodiments may include a composition comprising a therapeutically effective amount of nicotinamide riboside and a therapeutically effective amount of epsilon-viniferin; and a pharmaceutically acceptable excipient, wherein the composition is in a therapeutically effective amount for treatment of a neurodegenerative disorder.

Some embodiments may include a method comprising administering a therapeutically effective amount of nicotinamide riboside and a therapeutically effective amount of epsilon-viniferin for treatment of a neurodegenerative disorder in a patient in need of treatment thereof.

Some embodiments may include a composition comprising a therapeutically effective amount of nicotinamide riboside and a therapeutically effective amount of resveratrol; and a pharmaceutically acceptable excipient, wherein the composition is in a therapeutically effective amount for treatment of a neurodegenerative disorder.

Some embodiments may include a method comprising administering a therapeutically effective amount of nicotinamide riboside and a therapeutically effective amount of resveratrol for treatment of a neurodegenerative disorder in a patient in need of treatment thereof.

Some embodiment may include a composition as described herein used to regulate sirtuin deacetylase expression.

Certain embodiments may include a pharmaceutical composition comprising nicotinamide riboside, pterostilbene or a combination thereof for treating neurodegenerative disorders as described herein. In certain embodiments, the composition may comprise a therapeutically effective amount of nicotinamide riboside. In certain embodiments, the composition may comprise a therapeutically effective amount of pterostilbene. In certain embodiments, the composition will be provided on consecutive days and may be provided for at least a week, preferably at least two weeks, and most preferably at least a month.

Certain embodiments may include a dietary supplement composition comprising nicotinamide riboside, pterostilbene or a combination thereof for reducing the risk of neurodegenerative disorders as described herein. Certain embodiments may include a dietary supplement composition comprising nicotinamide riboside, pterostilbene or a combination thereof for reducing the risk of indicia of a neurodegenerative disorder as described herein. In certain embodiments, the composition may comprise an effective amount of nicotinamide riboside. In certain embodiments, the composition may comprise an effective amount of pterostilbene. In certain embodiments, the composition will be provided on consecutive days and may be provided for at least a week, preferably at least two weeks, and most preferably at least a month.

In certain embodiments, a composition as described herein can be used for diagnostic and/or predictive purposes. In such embodiments, differences in blood and/or brain NAD+ levels can be measured after administering compositions as described herein and comparing to known NAD+ levels in patients exhibiting neurodegenerative disorders, which can be compared to baseline levels to be used for diagnostic and/or predictive purposes. NAD+ brain levels can be measured via $^{31}P$ magnetic resonance spectroscopy.

In certain embodiments, a pharmaceutical composition may comprise a therapeutically effective amount of a combination of nicotinamide riboside and pterostilbene. A pharmaceutical composition can be in the form of a soft gel capsule or hard shell capsule, or other solid form such as a tablet. In certain embodiments, the pharmaceutical composition may contain about 250 mg of nicotinamide riboside and about 50 mg of pterostilbene. A pharmaceutical composition can be administered one or more times daily. In certain embodiments, the composition may be administered twice daily. In some embodiments where the pharmaceutical composition is administered twice daily, the composition may contain about 125 mg of nicotinamide riboside and about 25 mg of pterostilbene. In certain embodiments, the compounds, compositions or pharmaceutical compositions containing nicotinamide riboside and pterostilbene may be prepared as oral formulations.

Additional features, advantages, and embodiments of the invention are set forth or apparent from consideration of the following detailed description and claims. Moreover, it is to be understood that both the foregoing disclosure and the following description are exemplary and intended to provide further explanation without limiting the scope of any invention as claimed.

I. Definitions

The terms "patient", "subject", "individual" or "host" refer to either a human or a non-human animal.

The terms "treating" and "improving" mean that a neurodegenerative disorder and/or indicia of a neurodegenerative disorder is cured, lessened, reduced, improved, ameliorated, palliated, prevented, and/or reversed after administration. "Treating" and "improving" may also mean reducing the risk of indicia of a neurodegenerative disorder. "Treating" and "improving" may also mean reducing the risk of developing indicia of a neurodegenerative disorder. Curing, lessening, reducing, improving, ameliorating, palliating, preventing, and/or reversing indicia of a neurodegenerative disorder can be considered achievement of a desired therapeutic effect, or a desired effect from a dietary supplement. Indicia of a neurodegenerative disorder may include tremors including resting tremors, bradykinesia, NAD+ content such as but not limited to cellular NAD+ content, sirtuin activity, limb rigidity, Lewy bodies, postural instability, freezing of gait, micrographia, reduced facial expression, uncontrolled movements including movement that is abnormally fast or slow, stooped posture, dystonia, impaired fine motor dexterity and motor coordination, impaired gross motor coordination, decreased arm swing, akathisia, speech problems, softness of voice or slurred speech, difficulty swallowing, sexual dysfunction, cramping, drooling, excess saliva, loss of sense of smell, constipation, REM behavior disorder, mood disorder, orthostatic hypotension, sleep disturbances, vision problems, fatigue, loss of energy, depression, cognitive issues such as memory issues, slowed thinking, confusion, death of dopaminergic neurons, reduced dopamine concentration, prion occurrence, and dementia. "Treating", "treatment", 'improving", and "improvement" may be used interchangeably and their meaning as used herein will be clear to the skilled artisan. "Treating" and improving" may also refer to the reduction or elimination of other medication or medications administered to a patient, wherein that medication or medications is intended to cure, lessen, reduce, improve, ameliorate, palliate, prevent, and/or reverse a neurodegenerative disorder or indicia of a neurodegenerative disorder.

As used herein, the term "therapeutically effective" refers to the amount of nicotinamide riboside and/or pterostilbene or their equivalents needed to produce a desired therapeutic result. In certain embodiments, nicotinamide mononucleotide, niacinamide, nicotinamide, nicotinic acid and/or niacin may be substituted for nicotinamide riboside. In certain embodiments, a combination of nicotinamide riboside, nicotinamide mononucleotide, and/or niacin may be used. In certain embodiments epsilon-viniferin and/or resveratrol may be substituted for pterostilbene. In certain embodiments, a combination of pterostilbene, epsilon-viniferin, and/or resveratrol may be used.

As used herein, the term "effective" can refer to an amount of nicotinamide riboside and/or pterostilbene or their equivalents needed to produce a desired result. In certain embodiments, an effective amount may be an amount that achieves the result of maintaining a normal or healthy level of indicia of a neurodegenerative disorder. In certain embodiments, an effective amount can refer to an amount of nicotinamide riboside and/or pterostilbene or their equivalents needed to reduce the risk of indicia of a neurodegenerative disorder. An "effective" amount can also encompass a "therapeutically effective" amount depending upon the particular composition. The meaning of these terms will be clear to one of ordinary skill in the art when considering the claims and the context in which they are used.

As used herein, the term "pharmaceutically acceptable carrier" refers to a pharmaceutically-acceptable material, composition or vehicle, such as a liquid or solid filler, diluent, excipient, solvent or encapsulating material, involved in carrying or transporting any subject composition or component thereof.

As used herein, the term "acceptable carrier" can refer to an acceptable material, composition or vehicle, such as a liquid or solid filler, diluent, excipient, solvent or encapsulating material, involved in carrying or transporting any subject composition or component thereof.

As used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Stereoisomer", as used herein, refers to isomeric molecules that have the same molecular formula and sequence of bonded atoms (constitution), but which differ in the three dimensional orientations of their atoms in space. Examples of stereoisomers include enantiomers and diastereomers. As used herein, an enantiomer refers to one of the two mirror-image forms of an optically active or chiral molecule. A racemic mixture contains both forms of the optically active or chiral molecule. Diastereomers (or diastereoisomers) are stereoisomers that are not enantiomers (non-superimposable mirror images of each other). Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A mixture of enantiomers is referred to as a racemic mixture; which is typically 50:50 but that can differ due to the process of manufacture. A mixture of enantiomers can be enantiomerically enriched so that one enantiomer is present in an amount greater than 50%. Enantiomers and/or diastereomers can be resolved or separated using techniques known in the art.

"Substituted," as used herein, refers to all permissible substituents of the compounds or functional groups described herein. The permissible substituents can include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, which may be 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups. Such alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups can be further substituted.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups.

The term "formulation" may be used interchangeably with "composition" "dietary supplement" and/or "active agent." In certain embodiments, formulation may mean a combination of a composition and/or active agent and other aspects of embodiments described herein such as but not limited excipients. In certain embodiments, formulation may mean a combination of a composition and/or dietary supplement and other aspects of embodiments described herein such as but not limited acceptable carriers. The meaning of these terms will be clear to the skilled artisan based upon the context and their usage in the claims.

The term "dietary supplement" refers to a product intended to supplement the diet that comprises one or more dietary ingredients such as but not limited to nicotinamide riboside and/or pterostilbene. A dietary supplement is limited to products that are intended for ingestion in tablet, capsule, powder, softgel, gelcap, liquid, or other form of administration as described herein, that are not represented as conventional food or as the sole item of a meal or of the diet, and that are labeled as dietary supplements. In some embodiments a dietary supplement may be a composition that is in addition to the human diet and said composition is administered as disclosed herein, is not a natural or conventional food, meat or food flavoring or extract, or pharmaceutical product and that achieves desired effects such as improving the indicia of a neurodegenerative disorder.

In some embodiments, a straight chain or branched chain alkyl has 30 or fewer carbon atoms in its backbone (e.g., $C_1$-$C_{30}$ for straight chains, $C_3$-$C_{30}$ for branched chains), 20 or fewer, 15 or fewer, or 10 or fewer. Likewise, some cycloalkyls have from 3-10 carbon atoms in their ring structure, and may have have 5, 6 or 7 carbons in the ring structure. The term "alkyl" (or "lower alkyl") as used throughout the specification, examples, and claims can include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogens (such as fluorine, chlorine, bromine, or iodine), hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety, —NRR', wherein R and R' are independently hydrogen, alkyl, or aryl, and wherein the nitrogen atom is optionally quaternized; —SR, wherein R is hydrogen, alkyl, or aryl; —CN; —NO$_2$; —COOH; carboxylate; —COR, —COOR, or —CON(R)$_2$, wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, haloalkyl (such as —CF$_3$, —CH$_2$—CF$_3$, —CCl$_3$); —CN; —NCOCOCH$_2$CH$_2$, —NCOCOCHCH; —NCS; and combinations thereof.

Unless the number of carbons is otherwise specified, "lower alkyl" as used herein means an alkyl group, as defined above, but having from one to ten carbons, or one to six carbon atoms in its backbone structure. Likewise, "lower alkenyl" and "lower alkynyl" have similar chain lengths. Throughout the application, alkyl groups may be lower alkyls. In some embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Cycloalkyls can be substituted in the same manner.

The terms "alkenyl" and "alkynyl", refer to unsaturated aliphatic groups analogous in length and possible substitution to the alkyls described above, but that contain at least one double or triple bond respectively.

The term "substituted alkenyl" refers to alkenyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "substituted alkynyl" refers to alkynyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

"Aryl," as used herein, refers to $C_5$-$C_{26}$-membered aromatic, fused aromatic, fused heterocyclic, or biaromatic ring systems. "Aryl," as used herein, can include 5-, 6-, 7-, 8-, 9-, 10-, 14-, 18-, and 24-membered single-ring aromatic groups, for example, benzene, naphthalene, anthracene, phenanthrene, chrysene, pyrene, corannulene, coronene, etc. "Aryl" further encompasses polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles.

The term "substituted aryl" refers to an aryl group, wherein one or more hydrogen atoms on one or more aromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as CF$_3$, —CH$_2$—CF$_3$, —CCl$_3$), —CN, aryl, heteroaryl, and combinations thereof.

"Heterocycle," "heterocyclic" and "heterocyclyl" are used interchangeably, and refer to a cyclic radical attached via a ring carbon or nitrogen atom of a monocyclic or bicyclic ring containing 3-10 ring atoms, and can have from 5-6 ring atoms, comprising carbon and one to four heteroatoms each selected from the group consisting of non-peroxide oxygen, sulfur, and N(Y) wherein Y is absent or is H, O, $C_1$-$C_{10}$ alkyl, phenyl or benzyl, and optionally containing 1-3 double bonds and optionally substituted with one or more substituents. Heterocyclyl are distinguished from heteroaryl by definition. Examples of heterocycles include, but are not limited to piperazinyl, piperidinyl, piperidonyl, 4-piperidonyl, dihydrofuro[2,3-b]tetrahydrofuran, morpholinyl, piperazinyl, piperidinyl, piperidonyl, 4-piperidonyl, piperonyl, pyranyl, 2H-pyrrolyl, 4H-quinolizinyl, quinuclidinyl, tetrahydrofuranyl, 6H-1,2,5-thiadiazinyl. Heterocyclic groups can optionally be substituted with one or more substituents as defined above for alkyl and aryl.

The term "heteroaryl" refers to $C_5$-$C_{26}$-membered aromatic, fused aromatic, biaromatic ring systems, or combinations thereof, in which one or more carbon atoms on one or more aromatic ring structures have been substituted with a heteroatom. Suitable heteroatoms include, but are not limited to, oxygen, sulfur, and nitrogen. Broadly defined, "heteroaryl," as used herein, includes 5-, 6-, 7-, 8-, 9-, 10-, 14-, 18-, and 24-membered single-ring aromatic groups that may include from one to four heteroatoms, for example, pyrrole, furan, thiophene, imidazole, oxazole, thiazole, triazole, tetrazole, pyrazole, pyridine, pyrazine, pyridazine and pyrimidine, and the like. The heteroaryl group may also be referred to as "aryl heterocycles" or "heteroaromatics". "Heteroaryl" further encompasses polycyclic ring systems having two or more rings in which two or more carbons are common to two adjoining rings (i.e., "fused rings") wherein at least one of the rings is heteroaromatic, e.g., the other cyclic ring or rings can be cycloalkyls, cycloalkenyls, cycloalkynyls, aryls, heterocycles, or combinations thereof. Examples of heteroaryl rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, purinyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, tetrahydroisoquinolinyl, tetrahydroquinolinyl, tetrazolyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined below for "substituted heteroaryl".

The term "substituted heteroaryl" refers to a heteroaryl group in which one or more hydrogen atoms on one or more heteroaromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as CF₃, —CH₂—CF₃, —CCl₃), —CN, aryl, heteroaryl, and combinations thereof.

The term "heteroatom" as used herein means an atom of any element other than carbon or hydrogen. Exemplary heteroatoms include nitrogen, oxygen and sulfur.

"Analog" and "Derivative" may be used interchangeably, and refer to a compound that possesses the same core as the parent compound, but differs from the parent compound in bond order, the absence or presence of one or more atoms and/or groups of atoms, and combinations thereof. The derivative can differ from the parent compound, for example, in one or more substituents present on the core, which may include one or more atoms, functional groups, or substructures. In general, a derivative can be imagined to be formed, at least theoretically, from the parent compound via chemical and/or physical processes.

II. Compositions

A. Active Agents

Certain embodiments may comprise an active agent. An active agent may comprise one or more of the following in various combinations as would be understood by the skilled artisan.

An active agent comprising nicotinamide riboside and pterostilbene may be administered to a patient in a therapeutically effective amount, producing the unexpectedly superior results of achieving a synergistic and positive, self-reinforcing effect between an NAD+ dependent sirtuin activator compound (such as, but not limited to, pterostilbene) and NAD+ precursor that can supplement NAD+ concentration (such as, but not limited to, nicotinamide riboside). These effects may improve metabolic and mental health, thus reducing or eliminating certain neurodegenerative disorders and/or reducing, eliminating, or ameliorating the indicia of neurodegenerative disorders. In some embodiments, a composition may comprise nicotinamide riboside and pterostilbene in a therapeutically effective amount and this composition can achieve the unexpectedly superior results of creating a positive feedback loop as a result of cellular synergistic effects between nicotinamide riboside and pterostilbene, thus SIRT1-activators such as but not limited to pterostilbene could positively impact NAD+ production and concomitantly activate SIRT2-6 in addition to activating SIRT1. In certain embodiments as described herein, unexpectedly superior results can be achieved by providing optimal levels of sirtuin activity, while simultaneously normalizing any NAD+ deficiency.

Compositions as described herein can act as an agonist for peroxisome proliferator-activated receptor alpha (PPAR-alpha). PPAR-alpha agonists can exhibit neuroprotective benefits in animal models for neurodegenerative disorders such as but not limited to Parkinson's disease. Pterostilbene can demonstrate benefits in animal models for neurodegenerative disorders such as but not limited to Alzheimer's disease. Unexpectedly superior results may be achieved by providing predetermined levels of sirtuin activity along with PPAR-alpha activation as a result of administration of embodiments of compositions as described herein.

B. Dietary Supplements

Certain embodiments may comprise a dietary supplement. A dietary supplement may comprise one or more of the following in various combinations as would be understood by the skilled artisan.

A dietary supplement comprising nicotinamide riboside and/or pterostilbene in an effective amount may maintain normal or healthy levels of NAD+ concentration, maintain normal or healthy levels of sirtuin activity, and/or maintain normal or healthy levels of cellular detoxification in an individual. A dietary supplement comprising nicotinamide riboside and/or pterostilbene may be administered to an individual in an effective amount, producing the unexpectedly superior results of achieving a synergistic and positive, self-reinforcing effect between an NAD+ dependent sirtuin activator compound (such as, but not limited to, pterostilbene) and NAD+ precursor that can supplement NAD+ concentration (such as, but not limited to, nicotinamide riboside). These effects may reduce the risk of certain neurodegenerative disorders and/or reduce the risk of indicia of neurodegenerative disorders. In some embodiments, a composition may comprise nicotinamide riboside and pterostilbene in an effective amount and this composition can achieve the unexpectedly superior results of creating a positive feedback loop as a result of cellular synergistic effects between nicotinamide riboside and pterostilbene, thus SIRT1-activators such as but not limited to pterostilbene could positively impact NAD+ production and concomitantly activate SIRT2-6 in addition to activating SIRT1. In certain embodiments as described herein, unexpectedly superior results can be achieved by providing optimal levels of sirtuin activity, while simultaneously normalizing any NAD+ deficiency.

C. Nicotinamide Riboside

In certain embodiments, certain methods and compositions comprise nicotinamide riboside, a precursor of coenzyme NAD⁺, which is involved in metabolic processes such as energy production, DNA repair, cellular detoxification, the inflammatory response, and protein folding. The chemical structure of nicotinamide riboside is provided below.

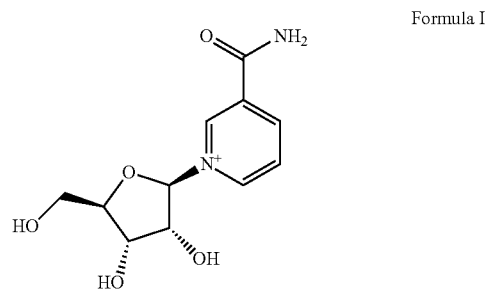 [SMILES: NC(=O)c1ccc[n+]([C@@H]2O[C@H](CO)[C@@H](O)[C@H]2O)c1]

Formula I

Nicotinamide riboside has four asymmetric centers and any optical isomer, as separated, pure or partially purified optical isomers and any mixtures thereof including racemic mixtures can be used in embodiments as described herein. The enantiomeric form can be in enantiomeric excess, e.g., essentially in a pure form. Accordingly, some embodiments comprise nicotinamide riboside having an enantiomeric excess of at least 60%, at least 70%, at least 80%, at least 85%, at least 90%, at least 96%, at least 98%, and ranges therebetween.

Racemic forms can be resolved into the optical antipodes by known methods, for example by separation of diastereomeric salts thereof with an optically active acid, and liberating the optically active amine compound by treatment with a base. Another method for resolving racemates into the optical antipodes is based upon chromatography on an optically active matrix. The compounds of embodiments of the invention may also be resolved by the formation of diastereomeric derivatives. Additional methods for the resolution of optical isomers, known to those skilled in the art, may be used. Such methods include those discussed by J. Jacques, A. Collet and S. Wilen in "Enantiomers, Racemates, and Resolutions", John Wiley and Sons, New York (1981). Optically active compounds can also be prepared from optically active starting materials.

Nicotinamide riboside can be a quaternary salt that can form an ionic bond with a counteranion. Examples of counteranions include the anions of a suitable organic acid such as formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutical acceptable inorganic or organic acid counteranions comprise the salts listed in J. Pharm. Sci. 66, 2 (1977)), which is incorporated by reference In certain embodiments, an active agent or a dietary supplement is a derivative, salt, solvate, or prodrug of nicotinamide riboside. In some embodiments, the riboside in nicotinamide riboside is (3-D-ribose. In certain embodiments, nicotinamide riboside may be substituted or combined with nicotinamide mononucleotide, niacinamide, nicotinamide, nicotinic acid, and/or niacin.

In some embodiments, an active agent or a dietary supplement has a chemical structure according to Formula I:

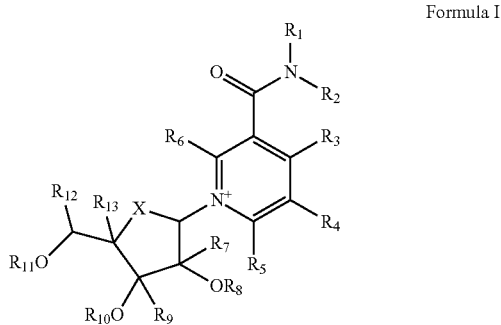

Formula I or is a pharmaceutically salt or acceptable salt thereof, wherein:

X is O, S, or NR;

$R_1$ and $R_2$ may be hydrogen, a substituted or unsubstituted alkyl group, a substituted or unsubstituted alkenyl group, a substituted or unsubstituted alkynyl group, a substituted or unsubstituted non-aromatic heterocyclic group or a substituted or unsubstituted aryl group;

$R_3$, $R_4$; $R_5$, $R_6$ and $R_7$ may be selected from the group consisting of hydrogen, a substituted or unsubstituted alkyl group, a substituted or unsubstituted aryl group, a substituted or unsubstituted non-aromatic heterocyclic group, halogen, —OR, —CN, —CO$_2$R, —OCOR, —OCO$_2$R, —C(O)NRR', —OC(O)NRR', —C(O)R, —COR, —SR, —OSO$_3$H, —S(O)$_n$R, —S(O)$_n$OR, —S(O)$_n$NRR', —NRR', —NRC(O)OR', —NO$_2$ and —NRC(O)R';

$R_8$, $R_{10}$, and $R_{11}$ may be selected from the group consisting of hydrogen, a substituted or unsubstituted alkyl group, a substituted or unsubstituted aryl group, —C(O)R, —C(O)OR, —C(O)NHR, —C(O)NRR', —S(O)$_n$R, —S(O)$_n$OR, —S(O)$_n$NRR', —C(S)R, —C(S)OR and —C(O)SR; and $R_9$, $R_{12}$, and $R_{13}$, may be selected from the group consisting of hydrogen, a substituted or unsubstituted alkyl group, a substituted or unsubstituted aryl group, a substituted or unsubstituted non-aromatic heterocyclic group, halogen, —CN, —CO$_2$R, —OCOR, —OCO$_2$R, —C(O)NRR', —OC(O)NRR', —C(O)R, —COR, —OSO$_3$H, —S(O)$_n$R, —S(O)$_n$OR, —S(O)$_n$NRR', —NRR', —NRC(O)OR', —NO$_2$ and —NRC(O)R';

wherein R and R' may be hydrogen, a substituted or unsubstituted alkyl group, a substituted or unsubstituted aryl group or a substituted or unsubstituted non-aromatic heterocyclic group; and n is 1 or 2. Compounds of Formula I may include isomers, enantiomers, and stereoisomers thereof.

D. Pterostilbene

An active agent may comprise pterostilbene. A dietary supplement may comprise pterostilbene. In certain embodiments, an active agent may comprise nicotinamide riboside and pterostilbene. In certain embodiments, a dietary supplement may comprise nicotinamide riboside and pterostilbene.

The chemical structure of pterostilbene is provided below:

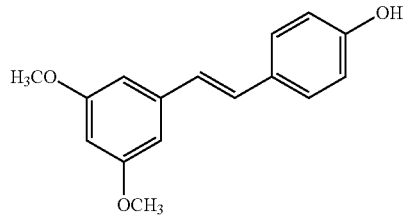 [SMILES: COc1cc(/C=C/c2ccc(O)cc2)cc(OC)c1]

In some embodiments, an active agent or a dietary supplement comprises a derivative, salt, solvate, or prodrug of pterostilbene. In certain embodiments, pterostilbene may be substituted and/or combined with epsilon-viniferin and/or resveratrol.

In certain other embodiments, the active agent or a dietary supplement is a stilbene having a chemical structure according to Formula II:

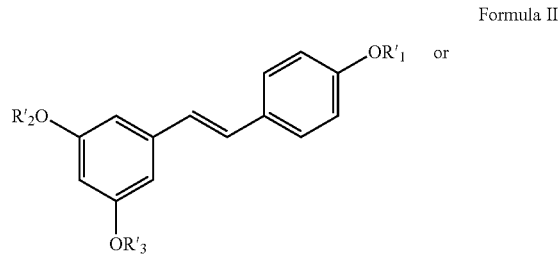

Formula II

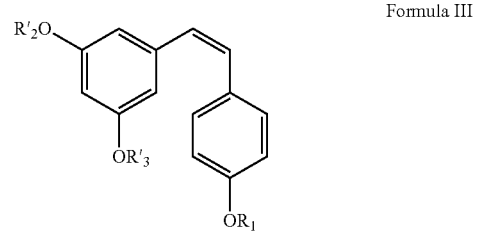

Formula III or is a pharmaceutically acceptable salt or acceptable salt thereof, wherein:

$R'_1$, $R'_2$, and $R'_3$ may be hydrogen, a substituted or unsubstituted alkyl group, a substituted or unsubstituted aryl group, —C(O)R, —C(O)OR, —C(O)NHR, —C(O)NRR', —S(O)$_n$R, —S(O)$_n$OR, —S(O)$_n$NRR', —C(S)R, —C(S)OR and —C(O)SR;

wherein R and R' may be hydrogen, a substituted or unsubstituted alkyl group, a substituted or unsubstituted aryl group or a substituted or unsubstituted non-aromatic heterocyclic group; and n is 1 or 2. Compounds of Formula II and Formula III may include isomers, enantiomers, and stereoisomers thereof.

E. Nicotinamide Mononucleotide

In certain embodiments, certain methods and compositions comprise nicotinamide mononucleotide, a precursor of coenzyme NAD$^+$, which is involved in metabolic processes such as energy production, DNA repair, cellular detoxification, the inflammatory response, and protein folding. The chemical structure of nicotinamide mononucleotide is provided below.

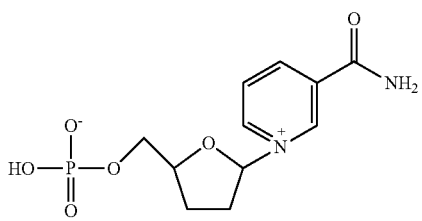

Nicotinamide mononucleotide has four asymmetric centers and any optical isomer, as separated, pure or partially purified optical isomers and any mixtures thereof including racemic mixtures can be used in embodiments as described herein. The enantiomeric form can be in enantiomeric excess, e.g., essentially in a pure form. Accordingly, some embodiments comprise nicotinamide riboside having an enantiomeric excess of at least 60%, at least 70%, at least 80%, at least 85%, at least 90%, at least 96%, at least 98%, and ranges there between.

Racemic forms can be resolved into the optical antipodes by known methods, for example by separation of diastereomeric salts thereof with an optically active acid, and liberating the optically active amine compound by treatment with a base. Another method for resolving racemates into the optical antipodes is based upon chromatography on an optically active matrix. The compounds of embodiments of the invention may also be resolved by the formation of diastereomeric derivatives. Additional methods for the resolution of optical isomers, known to those skilled in the art, may be used. Such methods include those discussed by J. Jacques, A. Collet and S. Wilen in "Enantiomers, Racemates, and Resolutions", John Wiley and Sons, New York (1981), which is incorporated by reference. Optically active compounds can also be prepared from optically active starting materials.

Nicotinamide mononucleotide can be a quaternary salt that can form an ionic bond with a counteranion. Examples of counteranions include the anions of suitable organic acid such as formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of acceptable inorganic or organic acid counteranions include the salts listed in J. Pharm. Sci. 66, 2 (1977)), which is incorporated by reference. In certain embodiments, an active agent or a dietary supplement is a derivative, salt, solvate, or prodrug of nicotinamide mononucleotide. In certain embodiments, nicotinamide mononucleotide may be substituted or combined with nicotinamide riboside, niacinamide, nicotinamide, nicotinic acid, and/or niacin.

In some embodiments, an active agent or a dietary supplement has a chemical structure according to Formula IV:

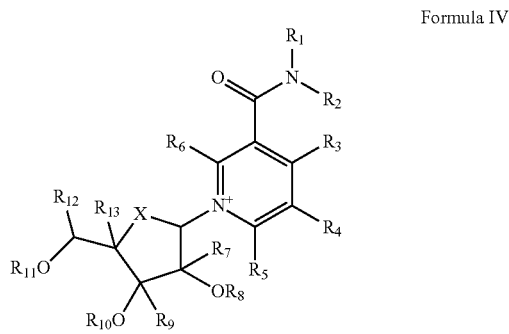

Formula IV or is a pharmaceutically acceptable salt or acceptable salt thereof, wherein:

X is O, S, or NR; —R$_1$ and R$_2$ may be hydrogen, a substituted or unsubstituted alkyl group, a substituted or unsubstituted alkenyl group, a substituted or unsubstituted alkynyl group, a substituted or unsubstituted non-aromatic heterocyclic group or a substituted or unsubstituted aryl group;

R$_3$, R$_4$, R$_5$, R$_6$ and R$_7$ may be selected from the group consisting of hydrogen, a substituted or unsubstituted alkyl group, a substituted or unsubstituted aryl group, a substituted or unsubstituted non-aromatic heterocyclic group, halogen, —OR, —CN, —CO$_2$R, —OCOR, —OCO$_2$R, —C(O)NRR', —OC(O)NRR', —C(O)R, —COR, —SR, —OSO$_3$H, —S(O)$_n$R, —S(O)$_n$OR, —S(O)$_n$NRR', —NRR', —NRC(O)OR', —NO$_2$ and —NRC(O)R';

R$_8$ and R$_{10}$ may be selected from the group consisting of hydrogen, a substituted or unsubstituted alkyl group, a substituted or unsubstituted aryl group, —C(O)R, —C(O)OR, —C(O)NHR, —C(O)NRR', —S(O)$_n$R, —S(O)$_n$OR, —S(O)$_n$NRR', —C(S)R, —C(S)OR and —C(O)SR;

R11 may be selected from the group consisting of hydrogen, a substituted or unsubstituted alkyl group, a substituted or unsubstituted aryl group, —P(O)$_n$, —P(O)$_n$R, —C(O)R, —C(O)OR, —C(O)NHR, —C(O)NRR', —S(O)$_n$R, —S(O)$_n$OR, —S(O)$_n$NRR', —C(S)R, —C(S)OR and —C(O)SR; and R$_9$, R$_{12}$, and R$_{13}$, may be selected from the group consisting of hydrogen, a substituted or unsubstituted alkyl group, a substituted or unsubstituted aryl group, a substituted or unsubstituted non-aromatic heterocyclic group, halogen. —CN, —CO$_2$R, —OCOR, —OCO$_2$R, —C(O)NRR', —NRR', —C(O)R, —COR, —OSO$_3$H, —S(O)$_n$R, —S(O)$_n$OR, —S(O)$_n$NRR', —NRR', —NRC(O)OR', —NO$_2$ and —NRC(O)R';

wherein R and R' may be hydrogen, a substituted or unsubstituted alkyl group, a substituted or unsubstituted aryl group or a substituted or unsubstituted non-aromatic heterocyclic group; and n is 1 or 2. Compounds of Formula IV may include isomers, enantiomers, and stereoisomers thereof.

F. Routes of Administration

In some embodiments, compounds, compositions, dietary supplements, and/or pharmaceutical compositions as described herein are formulated for oral delivery, i.e., in a formulation such as an oral formulation. Oral solid dosage forms are described generally in Remington's Pharmaceutical Sciences, 18$^{th}$ Ed. 1990 (Mack Publishing Co. Easton Pa. 18042) at Chapter 89, which is incorporated by reference in its entirety. Solid dosage forms comprise tablets, capsules, pills, troches or lozenges, cachets, pellets, powders, or granules or incorporation of the material into particulate preparations of polymeric compounds such as polylactic acid, polyglycolic acid, etc., or into liposomes. Such compositions may influence the physical state, stability, rate of in vivo release, and rate of in vivo clearance of the disclosed. See, e.g., Remington's Pharmaceutical Sciences, 18$^{th}$ Ed. (1990, Mack Publishing Co., Easton, Pa. 18042) pages 1435-1712, which in its entirety is incorporated by reference. Compositions of some embodiments may be prepared in liquid form, or may be in dried powder (e.g., lyophilized) form. Liposomal or proteinoid encapsulation may be used to formulate compositions as described herein. Liposomal encapsulation may be used and the liposomes may be derivatized with various polymers (e.g., U.S. Pat. No. 5,013,556, which is incorporated by reference). See also, Marshall, K. In: Modern Pharmaceutics Edited by G. S. Banker and C. T. Rhodes Chapter 10, 1979, which is incorporated by reference. A formulation may include a peptide (or chemically modified forms thereof) and inert ingredients that protect compounds in the stomach environment, and release of an active agent or a dietary supplement in the intestine.

Nicotinamide riboside, niacinamide, nicotinamide, nicotinic acid, pterostilbene, nicotinamide mononucleotide, niacin, epsilon-viniferin, resveratrol or derivatives thereof may be chemically modified so that oral delivery of an embodiment of the compound is therapeutically efficacious or efficacious to achieve a desired result as a dietary supplement. Contemplated chemical modification is the attachment of at least one moiety to the component molecule itself, where the moiety permits uptake into the blood stream from the stomach or intestine, or uptake directly into the intestinal mucosa. Also contemplated is the increase in overall stability of embodiments of the compositions described herein and increase in circulation time in the body. Certain embodiments may be pharmaceutical compositions. Certain embodiments may be dietary supplements.

Certain embodiments provide liquid dosage forms for oral administration, including pharmaceutically acceptable emulsions, solutions, suspensions, and syrups, which may contain other components including inert diluents; adjuvants such as wetting agents, emulsifying and suspending agents; and sweetening, and flavoring agents. Certain embodiments provide liquid dosage forms for oral administration, including acceptable emulsions, solutions, suspensions, and syrups, which may contain other components including inert diluents; adjuvants such as wetting agents, emulsifying and suspending agents; and sweetening, and flavoring agents suitable for use in dietary supplements.

Controlled release oral formulations may be provided in some embodiments. Controlled release may include, but is not limited to, delayed release and pH-dependent release. In certain embodiments, compositions as described herein, or derivatives thereof can be incorporated into microcapsules, microparticulates, nanoparticulates, etc. through use of release-altering agents such as coatings to affect release of at least one active agent. In certain embodiments, compositions as described herein, or derivatives thereof can be incorporated into an inert matrix which permits release by either diffusion or leaching mechanisms, e.g., gums. Slowly degenerating matrices may also be incorporated into compositions as described herein.

Modified release oral formulations may be provided. Modified release may allow for specific release profiles.

Extended release oral formulations may be provided. Extended release may allow for release of an active agent or dietary supplement over a desired time period.

Additional discussions for varying release formulations and related terms may be found in Lesczek Krowczynski, *Extended-Release Dosage Forms,* 1987 (CRC Press, Inc.), which is incorporated by reference.

In certain embodiments, the form of a controlled, modified or extended release oral formulation is a tablet, capsule, or microbeads for oral administration. In other aspects, controlled, modified or extended release formulations comprising suitable and effect treatment amounts of the desired components may be pills, powders, granules, sterile parenteral solutions or suspensions, oral solutions or suspensions, oil water emulsions as well as implants and microencapsulated delivery systems.

Embodiments of some formulations may provide controlled, modified or extended release profiles. Compositions of embodiments of the present invention may comprise a conventional binder, excipients and additives, which may act to control, modify or extend release when used in sufficient quantities. Certain embodiments comprise a pharmaceutical binder, excipient, and/or additive, which may act to control, modify or extend release when used in sufficient quantities. Coating agents, e.g., plasticizers, may be used to enhance the controlled, modified or extended release features of embodiments of compositions of the invention.

For oral formulations, the location of release may be the stomach, the small intestine (the duodenum, the jejunum, or the ileum), or the large intestine. Such a release can avoid the deleterious effects of the stomach environment, either by protection of at least one active agent (or derivative) or by release of at least one active agent or dietary supplement (or derivative) beyond the stomach environment, such as in the intestine. To ensure full gastric resistance a coating temporally impermeable to at least pH 5.0 is useful in some embodiments. Examples of some inert ingredients that are used as enteric coatings are cellulose acetate trimellitate (CAT), hydroxypropylmethylcellulose phthalate (HPMCP), polyvinyl acetate phthalate (PVAP), poly(methacrylic acid-co-ethyl acrylate) 1:1, cellulose acetate phthalate (CAP), poly(methacylic acid-co-methyl methacrylate) 1:1, poly (methacylic acid-co-methyl methacrylate) 1:2, and natural shellac resin. In some embodiments, coatings may be used as mixed films.

i. Soft or Hard Gel Capsules

Certain embodiments utilize oral administration of soft capsules comprising nicotinamide riboside and/or pterostilbene or embodiments of compositions as described herein. Some embodiments of methods comprise administering a capsule comprising an effective amount of nicotinamide riboside and/or pterostilbene, or embodiments of compositions as described herein. A capsule can be a hard capsule or a soft capsule. A soft capsule can be prepared using techniques well known in the art. For example, soft capsules can be produced using a rotary die encapsulation process. Active agent or dietary supplement formulations can be fed into an encapsulation machine by gravity. In some embodiments, a formulation comprises pharmaceutical and/or dietary supplement excipients such as olive oil, gelatin, glycerin, purified water, beeswax yellow, sunflower lecithin, silicon dioxide, titanium dioxide, F. D. & C Blue 1 and F. D. & C Red 4, microcrystalline cellulose, hypromellose, vegetable magnesium stearate, and/or silica.

A capsule shell can comprise one or more plasticizers such as glycerin, sorbitol, sorbitans, maltitol, glycerol, polyethylene glycol, polyalcohols with 3 to 6 carbon atoms, citric acid, citric acid esters, triethyl citrate and combinations thereof. In some embodiments, a plasticizer can be glycerin.

In addition to plasticizer(s), a capsule shell can comprise other suitable shell additives such as opacifiers, colorants, humectants, preservatives, flavorings, and buffering salts and acids.

Opacifiers can be used to opacify a capsule shell when an encapsulated active agent(s) is light sensitive. Suitable opacifiers include, but not limited to, titanium dioxide, zinc oxide, calcium carbonate and combinations thereof. In some embodiments, the opacifier can be titanium dioxide.

Colorants can be used to for marketing and product identification and/or differentiation purposes. Suitable colorants include synthetic and natural dyes and combinations thereof.

Humectants can be used to suppress the water activity of a softgel. Suitable humectants include but are not limited to glycerin and sorbitol, which can be components of a plasticizer composition. Due to the low water activity of dried, properly stored softgels, the greatest risk from microorganisms comes from molds and yeasts. For this reason, preservatives can be incorporated into some embodiments of a capsule shell. Suitable preservatives include but are not limited to alkyl esters of p-hydroxy benzoic acid such as methyl, ethyl, propyl, butyl and heptyl (collectively known as "parabens") or combinations thereof.

In certain embodiments, a composition comprises nicotinamide riboside and pterostilbene as active agents or dietary supplements. Some embodiments can be in a capsule formed of microcrystalline cellulose, hypromellose, vegetable magnesium stearate, olive oil, gelatin, glycerin, purified water, beeswax yellow, sunflower lecithin, silicon dioxide, titanium dioxide, F. D. & C Blue 1 and F. D. & C Red 4, or vegetarian hard capsules made solely of plant materials. Any embodiment as described herein may include microcrystalline cellulose, hypromellose, vegetable magnesium stearate, and/or silica.

Other excipients (which can be pharmaceutical excipients in some embodiments) that can be included in the disclosed formulations, include acetyl-L-carnitine, N-acetyl cysteine, α-lipoic acid, biotin, thiamine, pantothenic acid, vitamin B6, vitamin B12, vitamin K, taurine, folic acid, resveratrol, vinpocetine, chromium picolinate, vitamin C, vitamin D3, vitamin E, vinaringin, quercetin, curcumin, coenzyme Q, creatine and salts thereof.

ii. Solutions and Suspensions

Certain embodiments can comprise a composition administered as a liquid with an active agent or a dietary supplement dissolved (e.g., solution) or dispersed (e.g., suspension) in the composition. The solution or suspension may be prepared using one or more acceptable excipient and/or pharmaceutically acceptable excipients. Suitable excipients include, but are not limited to, surfactants, humectants, plasticizers, crystallization inhibitors, wetting agents, bulk filling agents, solubilizers, bioavailability enhancers, pH adjusting agents, flavorants and combinations.

iii. Controlled Delivery Polymeric Matrices

Controlled release polymeric devices can be made for long term release systemically following implantation of a polymeric device (rod, cylinder, film, disk), injection or oral ingestion (microparticles). A polymeric device matrix can be in the form of microparticles such as microspheres, where peptides can be dispersed within a solid polymeric matrix or microcapsules, where the core can be of a different material than the polymeric shell, and the peptide can be dispersed or suspended in the core, which may be liquid or solid in nature. Unless specifically defined herein, microparticles, microspheres, and microcapsules can be used interchangeably. A polymer matrix may be cast as a thin slab or film, ranging from nanometers to four centimeters, a powder produced by grinding or other standard techniques, or even a gel such as a hydrogel.

Non-biodegradable or biodegradable matrices can be used for delivery of disclosed compounds, although biodegradable matrices are present in certain embodiments. These may be natural or synthetic polymers, although synthetic polymers may be used in certain embodiments for characterization of degradation and release profiles. A polymer can be selected based on the period over which release is desired. In some cases linear release may be most useful, although in others a pulse release or "bulk release" may provide more effective results. In certain embodiments, the polymer may be in the form of a hydrogel (typically in absorbing up to about 90% by weight of water), and can optionally be crosslinked with multivalent ions or polymers.

Polymeric device matrices can be formed by solvent evaporation, spray drying, solvent extraction and other methods known to those skilled in the art. Bioerodible microspheres can be prepared using any of the methods developed for making microspheres for drug delivery (which can also be used for dietary supplements), for example, as described by Mathiowitz and Langer, *J. Controlled Release* 5:13-22 (1987); Mathiowitz, et al., *Reactive Polymers* 6:275-283 (1987); and Mathiowitz, et al., *J. Appl. Polymer Sci.* 35:755-774 (1988) both of which are incorporated by reference in their entirety.

Polymeric devices can be formulated for local release to treat the area of implantation or injection—which can deliver a dosage that is much less than the dosage for treatment of an entire body—or systemic delivery. Some of these embodiments can be implanted or injected subcutaneously, into the muscle, fat, or swallowed.

G. Dosages and Dosage Regiments

Selection of embodiments of a particular therapeutically effective dose or an effective dose can be determined (e.g. but not limited to, via clinical trials) by a skilled artisan based upon the consideration of several factors which will be known to one of skill in the art. Such factors include the disorder to be treated, prevented, reduction of indicia of neurodegenerative disorders, the symptoms involved, the subject's body mass, the subject's age, the subject's immune status and other factors known by the skilled artisan. The precise dose to be employed in the formulation will also depend on the route of administration, and the seriousness of the disorder-related wasting, and should be decided according to the judgment of the skilled artisan and each subject's circumstances. Effective doses can be extrapolated from dose-response curves derived from in vitro or animal model test systems.

The dose of the active agent or the dietary supplement to be administered to a subject, such as a human, can be variable and can be subject to independent judgment. It is often practical to administer the daily dose of the active agent or dietary supplement at various hours of the day. The amount of the active agent or dietary supplement administered may depend on such factors as the solubility of the active agent or dietary supplement, the formulation used, subject condition (such as weight), and/or the route of administration. In certain embodiments, a dose of administered nicotinamide riboside or its equivalents, alone or in combination with pterostilbene or its equivalents is administered orally.

Effective amounts of administered nicotinamide riboside or its equivalents, alone or in combination with pterostilbene or its equivalents, can be in an amount of between about 50 mg and about 1500 mg, between about 100 mg and about 1500 mg, between about 100 mg and about 1000 mg per day, between about 125 mg and about 900 mg per day, between about 150 mg and about 850 mg per day, between about 200 mg to 700 mg per day, between about 200 mg to about 500 mg per day, about 250 mg per day, between about 1000 mg and about 1500 mg, or 250 mg per day. In certain embodiments, an effective amount of nicotinamide riboside or its equivalents may be administered via multiple doses.

An effective amount of administered pterostilbene or its equivalents, alone or in combination with nicotinamide riboside or its equivalents, can be in an amount between about 25 mg and about 1000 mg, between about 100 mg and about 1000 mg, between about 25 mg and about 500 mg per day, between about 25 mg and about 250 mg per day, between about 30 mg and about 225 mg per day, between about 40 mg and about 200 mg per day, between about 45 mg and about 250 mg per day, about 50 mg per day, or about 50 mg per day. In certain embodiments, an effective amount of pterostilbene or its equivalents may be administer via multiple doses. In an embodiment, the compounds, compositions, dietary supplements, or pharmaceutical compositions containing nicotinamide riboside and pterostilbene are prepared as oral formulations.

In certain embodiments a composition may be administered in a dosage regimen over days, weeks, or months. Dosages may be multiple times per day or singular doses per day. Each dosage when dosages are administered over multiple days, weeks, or months may or may not be equal amounts. Dosage amounts during a dosage regimen may vary according to the amounts and ranges disclosed herein. A dosage may comprise administering nicotinamide riboside alone or in combination with pterostilbene. A dosage may comprise administering pterostilbene alone or in combination with nicotinamide riboside.

In certain embodiments, a composition as disclosed herein can be administered intravenously, intraperitoneally, subcutaneously, intramuscularly, intrathecally, sublingually, into the buccal cavity, rectally, or by aerosol.

III. Methods of Use

Certain compositions and methods described herein may have beneficial effects on symptoms associated with neurodegenerative disorders. Certain compositions and methods described herein may treat and/or prevent neurodegenerative disorders. Certain compositions may maintain normal or healthy levels of indicia of neurodegenerative disorders. Certain compositions may reduce the risk of developing indicia of neurodegenerative disorders. Certain compositions may reduce the risk of indicia of neurodegenerative disorders. Certain compositions described herein may be oral compositions to provide oral formulations for treating and/or preventing neurodegenerative disorders. Certain compositions and methods described herein may improve and/or maintain an aesthetic appearance of neurodegenerative disorder. In some embodiments, a composition may treat and/or prevent a neurodegenerative disorder. Some embodiments may be a pharmaceutical ingredient and others may be a dietary supplement.

Neurodegenerative disorders that can be treated include, but are not limited to, those associated with aging, Parkinson's disease, Alzheimer's disease, dementia, and diabetes. A dietary supplement may reduce the risk of developing indicia of these neurodegenerative disorders. Neurodegenerative disorders that are treated may or may not exclude those associated with aging, Parkinson's disease, Alzheimer's disease, Huntington's disease, and dementia, as will be indicated in the claims.

In some embodiments, a neurodegenerative disorder treated with embodiments of the described compositions and methods include, but are not limited to Parkinson's disease, Alzheimer's disease, and Huntington's disease.

In certain embodiments, a composition as described herein can be used to reduce dosage levels of dopamine agonists, monoamine oxidase inhibitors, and/or levodopa and the like. Other medications administered to a patient having Parkinson's disease that can have dosage levels reduced would be readily ascertainable to the skilled artisan. In certain embodiments, compositions as described herein can be administered to a patient to treat Parkinson's disease. In certain embodiments, compositions as described herein can be administered to a patient to treat indicia of Parkinson's disease. In certain embodiments, compositions as described herein may be administered to increase activation of heat shock factor 1.

The present invention will be further understood by reference to the following non-limiting examples.

EXAMPLES

Example 1: Exemplary Composition

Materials: One Composition is the Product Marketed by Elysium Health as "BASIS®".

TABLE 1

| Active Components of BASIS ® | |
| --- | --- |
| Component | Weight of component |
| Nicotinamide riboside | 250 mg |
| Pterostilbene | 50 mg |

BASIS® may further contain the following excipients: microcrystalline cellulose, hypromellose, vegetable magnesium stearate, olive oil, gelatin, glycerin, purified water, beeswax yellow, sunflower lecithin, silicon dioxide, titanium dioxide, F. D. & C Blue 1 and F. D. & C Red 4. Any embodiment may include microcrystalline cellulose, hypromellose, vegetable magnesium stearate, and/or silica.

Example 2: Mouse Model

In an embodiment, Parkinson's model mice (e.g., mice systemically injected with 1-methyl 4-phenyltetrahydropyridine (MPTP)) will be used and will be treated using the following treatments:

The test mice will be broken into four groups:
1. Control (no treatment);
2. Treatment with nicotinamide riboside (NR), nicotinamide mononucleotide (NMN) and combinations thereof;
3. Treatment with NR, NMN, pterostilbene, and combinations thereof;

4. Pterostilbene treated;

5. Mice treated with NR, NMN and combinations thereof, and pterostilbene

Mice will be treated daily for three weeks, and specific assays will be carried out to determine whether indicia of neurodegenerative disorders have been improved. These assays will include, but not be limited to, testing mouse sensorimotor function including but not limited to, neurochemical assay of using tyrosine hydroxylase, behavioral testing such as rotational bias, testing of motor functions such as turning ability and reaching ability, testing sensory stimuli, responses to light, and the like.

For this example, the viability of the dopaminergic neurons will be scored by staining appropriate brain sections for tyrosine hydroxylase.

Doses of NR and NMN will be about 250 mg/kg body weight of mice/daily. Doses of pterostilbene will be about 100 mg/kg body weight of mice/daily. Doses of NR, NMN and combinations thereof, and pterostilbene will be about 250 mg/kg body weight of mice/daily. NR, NMN, pterostilbene and combinations thereof will be administered by intraperitoneal (IP) injection or by supplementing the food or the water.

Example 3: Transgenic Mouse Model

In an embodiment, a transgenic mouse model (e.g., alpha synuclein transgenic mice) will be used and will be treated using the following treatments:

The test mice will be broken into four groups:

1. Control (no treatment);

2. Treatment with nicotinamide riboside (NR), nicotinamide mononucleotide (NMN) and combinations thereof;

3. Treatment with NR, NMN, pterostilbene, and combinations thereof;

4. Pterostilbene treated;

5. Mice treated with NR, NMN and combinations thereof, and pterostilbene

Mice will be treated daily for three weeks, and specific assays will be carried out to determine whether indicia of neurodegenerative disorders have been improved. These assays will include, but not be limited to, testing mouse sensorimotor function including but not limited to, neurochemical assay of using tyrosine hydroxylase, behavioral testing such as rotational bias, testing of motor functions such as turning ability and reaching ability, testing sensory stimuli, responses to light, and the like.

For these transgenic mice, measured endpoints will be survival rates of the treated transgenic mice that will be compared to untreated transgenic mice (i.e., Tg/Tg mice typically live about 6 months), and assays will be conducted to test for physical strength and dexterity, such as on a rotarod and/or treadmill.

Doses of NR and NMN will be about 250 mg/kg body weight of mice/daily. Doses of pterostilbene will be about 100 mg/kg body weight of mice/daily. Doses of NR, NMN and combinations thereof, and pterostilbene will be about 250 mg/kg body weight of mice/daily. NR, NMN, pterostilbene and combinations thereof will be administered by intraperitoneal (IP) injection or by supplementing the food or the water.

Example 4: Results of Human Administration

In an embodiment, human subjects will be given a dosage of about 500 mg/day of NR and/or NMN. Human subjects may also be given about 100 mg/day of pterostilbene. Some subjects will be given a dose 500 mg nicotinamide riboside and 100 mg of pterostilbene for 60 days for the treatment of indicia of Parkinson's disease. Subjects are to be grouped based upon certain indicia of neurodegenerative disorders, such as Parkinson's disease. Several of the symptoms described herein will be monitored and their indicia will be improved. Each participant will also self-report using a survey that will contain questions related to indicia of symptoms of a neurodegenerative disorder. The trial will be placebo-controlled, randomized and blinded.

A reduction in the indicia of Parkinson's disease will be observed. A reduction in Parkinson's disease medication L-DOPA will be reduced. Subjects will also be tested to see responses in tremor reduction, increases in mental cognition, memory increase, and the like.

Unless defined otherwise, all technical and scientific terms used herein have the same meanings as commonly understood by one of skill in the art to which the disclosed invention belongs. Publications cited herein and the material for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

Although the foregoing description is directed to preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

We claim:

1. A method of reducing the prevalence of indicia of a neurodegenerative disease in a subject in need thereof comprising administering to the subject a composition consisting of nicotinamide riboside, pterostilbene and a pharmaceutically acceptable carrier and/or excipient, wherein the composition is administered to the subject daily, and the daily dose of nicotinamide riboside is between 200 mg to 700 mg and the daily dose of pterostilbene is between 45 mg to 250 mg.

2. The method of claim 1, wherein the indicia of a neurodegenerative disease are tremors, resting tremors, bradykinesia, NAD+ content, sirtuin activity, limb rigidity, Lewy bodies, postural instability, freezing of gait, micrographia, reduced facial expression, uncontrolled movements, movement that is abnormally fast or slow, stooped posture, dystonia, impaired fine motor dexterity, impaired motor coordination, impaired gross motor coordination, decreased arm swing, akathisia, speech problems, softness of voice or slurred speech, difficulty swallowing, sexual dysfunction, cramping, drooling, excess saliva, loss of sense of smell, constipation, rapid eye movement (REM) behavior disorder, mood disorder, orthostatic hypotension, sleep disturbances, vision problems, fatigue, loss of energy, depression, memory issues, slowed thinking, confusion, death of dopaminergic neurons, reduced dopamine concentration, prion occurrence, or dementia.

3. The method of claim 1, wherein the neurodegenerative disease is Alzheimer's disease, Parkinson's disease, or Huntington's disease.

4. The method of claim 1, wherein the administration of the composition comprises administering one or more doses of the composition.

5. The method of claim 4, wherein two or more, thirty or more, fifty or more, or one hundred or more doses of the composition are administered.

6. The method of claim 4, wherein the doses are administered for at least 7 days, at least 30 days, at least 60 days, at least 90 days, or at least six months.

7. The method of claim 1, wherein the composition is formulated as a pill, a tablet, or a capsule.

8. The method of claim 1, wherein the composition is administered orally.

9. The method of claim 1, wherein the composition is self-administered.

10. A method of reducing the prevalence of indicia of a neurodegenerative disease in a subject in need thereof comprising administering to the subject a composition consisting of nicotinamide riboside, pterostilbene and a pharmaceutically acceptable carrier or excipient, wherein the composition is administered to the subject daily, and the daily dose of nicotinamide riboside is 500 mg and the daily dose of pterostilbene is 100 mg.

* * * * *